United States Patent
Jung et al.

(12)

(10) Patent No.: US 6,348,296 B1
(45) Date of Patent: Feb. 19, 2002

(54) COPOLYMER RESIN, PREPARATION THEREOF, AND PHOTORESIST USING THE SAME

(75) Inventors: Min Ho Jung; Cha Won Koh; Hyung Gi Kim, all of Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 237 days.

(21) Appl. No.: 09/223,662

(22) Filed: Dec. 30, 1998

(30) Foreign Application Priority Data

Dec. 31, 1997 (KR) ............................................ 97-81343

(51) Int. Cl.$^7$ ................................................. G03C 1/76
(52) U.S. Cl. .................... 430/270.1; 560/120; 522/113; 526/318
(58) Field of Search ...................... 560/120; 430/270.1; 522/113; 526/318

(56) References Cited

U.S. PATENT DOCUMENTS

| | | | | |
|---|---|---|---|---|
| 4,106,943 A | * | 8/1978 | Ikeda et al. ............... | 430/288.1 |
| 5,212,043 A | * | 5/1993 | Yamamoto et al. .......... | 430/192 |
| 6,045,967 A | * | 4/2000 | Jung et al. ................ | 430/270.1 |
| 6,132,926 A | | 10/2000 | Jung et al. ................ | 430/270.1 |

FOREIGN PATENT DOCUMENTS

GB          1407069          *   9/1975

OTHER PUBLICATIONS

ACS Abstract Ref. 172992–05–1.
ACS Abstract Ref. 172992–04–1.
CA Ref. No. 1996: 58168 Chem. Mater. (1996), 8(2), pp. 440–447.
CA Ref. No. 1996:58162 Chem. Mater. (1996), 8(2), pp. 376–381.
U.S. Ser. No. 09/222,053, Jung et al., filed Dec. 29,1998.

* cited by examiner

*Primary Examiner*—Gary Geist
*Assistant Examiner*—Taylor Victor Oh
(74) *Attorney, Agent, or Firm*—Townsend and Townsend and Crew LLP

(57) ABSTRACT

The present invention relates to a copolymer resin for a photoresist used with ultra-short wavelength light source such as KrF or ArF, a process for preparation thereof, and a photoresist comprising said resin. By introducing 2,3-di-t-butyl-5-norbornene-2,3-dicarboxylate unit into the structure of a norbornene-maleic anhydride copolymer, the copolymer resin according to the present invention is easily prepared by conventional radical polymerization, has high transparency at 193 nm wavelength, provides increased etching resistance, prevents the top loss phenomenon, exhibits enhanced adhesive strength due to increasing protection ratio in the copolymer resin, and shows excellent resolution.

15 Claims, No Drawings

COPOLYMER RESIN, PREPARATION THEREOF, AND PHOTORESIST USING THE SAME

BACKGROUND OF THE INVENTION

1. Field of the Invention

The present invention relates to a copolymer resin for a photoresist used with an ultra-shortwave light source such as KrF or ArF, a process for preparation thereof, and a photoresist using the same. More specifically, it relates to a photoresist resin wherein a 2,3-t-butyl-5-norbornene-2,3-dicarboxylate unit has been introduced into a norbornene-maleic anhydride copolymeric structure. The photoresist is preferably used in lithography processes using KrF(248 nm) or ArF(193 nm) light sources which are typically used in the manufacture of 1G or 4G Dynamic Random Access Memory ("DRAM") semi-conductor integrated circuits.

2. Description of the Prior Art

In general, etching resistance, adhesiveness, and low light absorption at 193 nm wavelength are required for a copolymer resin to be useful as a photoresist for ArF light sources. The copolymer resin is also preferably developable by using 2.38 wt % aqueous tetramethylammonium hydroxide (TMAH) solution. However, it is very difficult to synthesize a copolymer resin satisfying all these properties. Up to the present time, many researchers have focused their studies on novolac type resins to increase transparency at 193 nm wavelength and increase etching resistance. Researchers at Bell Labs have tried to introduce an alicyclic unit to the backbone chain of the copolymer resin in order to enhance etching resistance. For example, a copolymer resin has been suggested in which the backbone chain has norbornene, acrylate and maleic anhydride substituents, as represented by the following Formula I:

[FORMULA I]

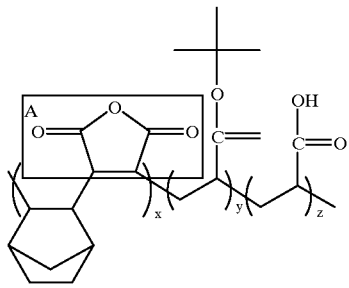

In the copolymer resin of Formula I, the maleic anhydride portion (identified by the letter A) is used for polymerizing the alicyclic olefin unit. However, the maleic anhydride portion is very soluble in 2.38% aqueous TMAH solution, even if it has not been exposed to the ArF light source, so that 'top loss' phenomenon (the top of the pattern being formed in a round shape) occurs in practical photoresist patterning. Thus, the copolymer resin of Formula I cannot be used as a photoresist for ArF sources.

In order to prevent such dissolution, it has been proposed to greatly increase the value of "y" in Formula I, thereby increasing the tert-butyl substituent. However, an increase in "y" causes a relative decrease in the value of "z". The relative decrease of the "z" portion, which enhances sensitivity and adhesiveness with the substrate, causes disadvantages in practical patterning in that the photoresist tends to be removed from the wafer so that a pattern cannot be formed.

SUMMARY OF THE INVENTION

In accordance with one aspect of the present invention, a 2,3-di-t-butyl-5-norbornene-2,3-dicarboxylate unit having two protective groups is introduced into a norbornene-maleic anhydride copolymer structure, resulting in a copolymer resin having a high transparency at 193 nm wavelength and high etching resistance. The copolymers of the present invention can be easily prepared by conventional radical polymerization, and prevent top loss phenomenon, exhibit enhanced adhesive strength and show excellent resolution of 0.13 $\mu$m in patterning applications.

It is an object of the present invention to provide a copolymer resin comprising a 2,3-di-t-butyl-5-norbornene-2,3-dicarboxylate unit.

It is another object of the present invention to provide a process for preparing the copolymer resin comprising a 2,3-di-t-butyl-5-norbornene-2,3-dicarboxylate unit.

It is still another object of the present invention to provide a photoresist comprising the above norbornene-maleic anhydride copolymer resin.

It is still further object of the present invention to provide a semiconductor element manufactured by using the above copolymer resin as a photoresist.

DETAILED DESCRIPTION OF THE INVENTION

The present invention relates to a copolymer resins comprising a 2,3-di-t-butyl-5-norbornene-2,3-dicarboxylate unit, represented by the following Formula III:

[FORMULA III]

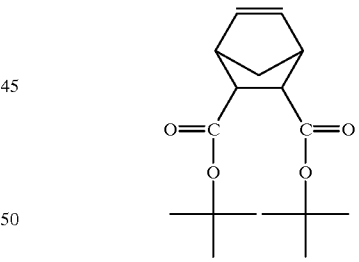

The copolymer resins according to the present invention preferably include the following norbornene-maleic anhydride copolymer resins:

(1) Poly[2,3-di-t-butyl-5-norbornene-2,3-dicarboxylate/
2-hydroxyethyl-5-norbornene-2-carboxylate/maleic anhydride/5-norbornene-2-carboxylic acid] copolymer resin (molecular weight: 3,000–100,000) having the following Formula IV:

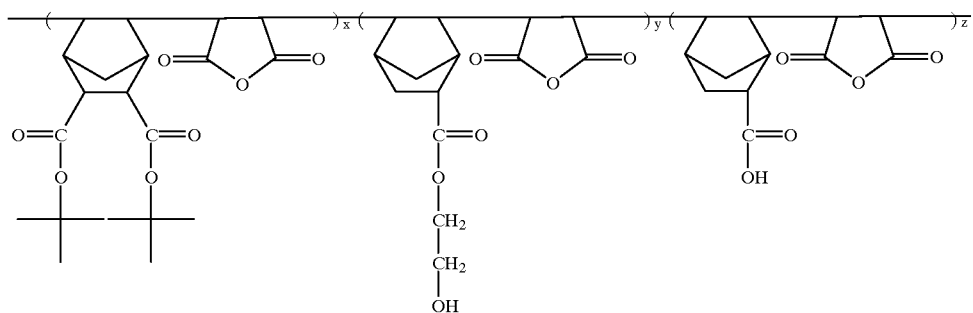

[FORMULA IV]

wherein, the ratio x:y:z is (0.001–99%):(0–99%): (0–99%);

(2) Poly[2,3-di-t-butyl-5-norbornene-2,3-dicarboxylate/ 2-hydroxyethyl-5-norbornene-2-carboxylate/maleic anhydride/mono-methyl cis 5-norbornene-endo-2,3-dicarboxylic acid] copolymer resin (molecular weight: 3,000–100,000) having the following Formula V;

wherein, x is a mole % of 0.001–99%, more preferably is 0.5–99%, and y and z are independently a mole % of 0.1–99%; and (4) Poly[2,3-di-t-butyl-5-norbornene-2,3-dicarboxylate/ 2-hydroxypropyl-5-norbornene-2-carboxylate/maleic anhydride/mono-methyl cis 5-norbornene-endo-2,3-dicarboxylate] copolymer resin (molecular weight: 4,000–100,000) having the following

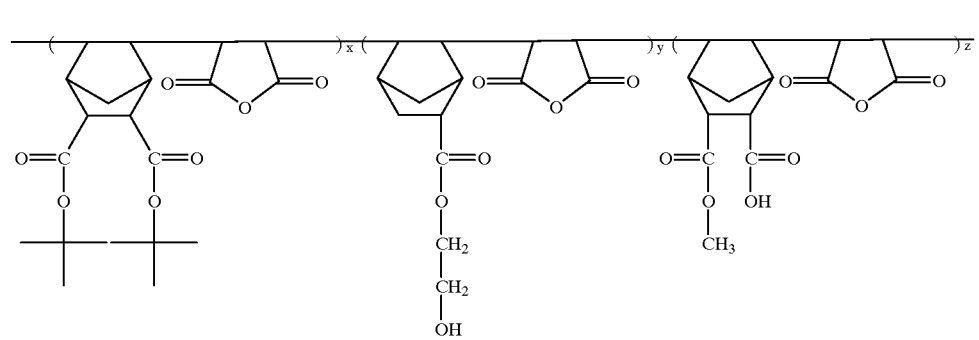

[FORMULA V]

wherein, the ratio x:y:z is (0.001–99%): (0–99%): (0–99%);

(3) Poly[2,3-di-t-butyl-5-norbornene-2,3-dicarboxylate/ 2-hydroxypropyl-5-norbornene-2-carboxylate/maleic anhydride/5-norbornene-2-dicarboxylic acid] copolymer resin (molecular weight: 4,000–100,000) having the following Formula VI:

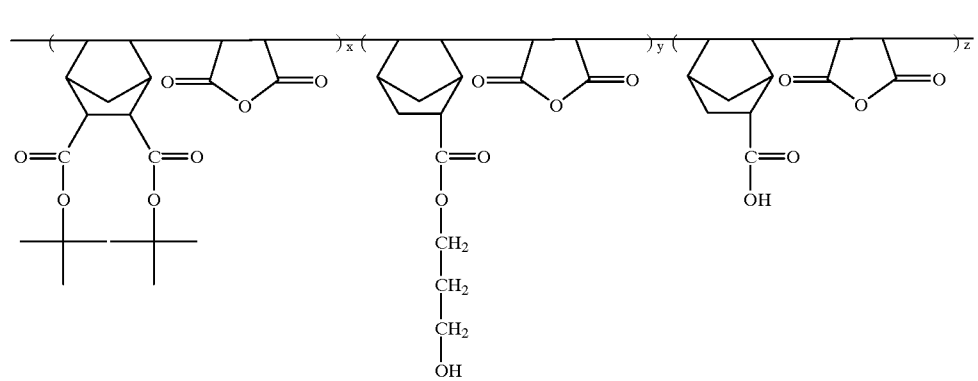

[FORMULA VI]

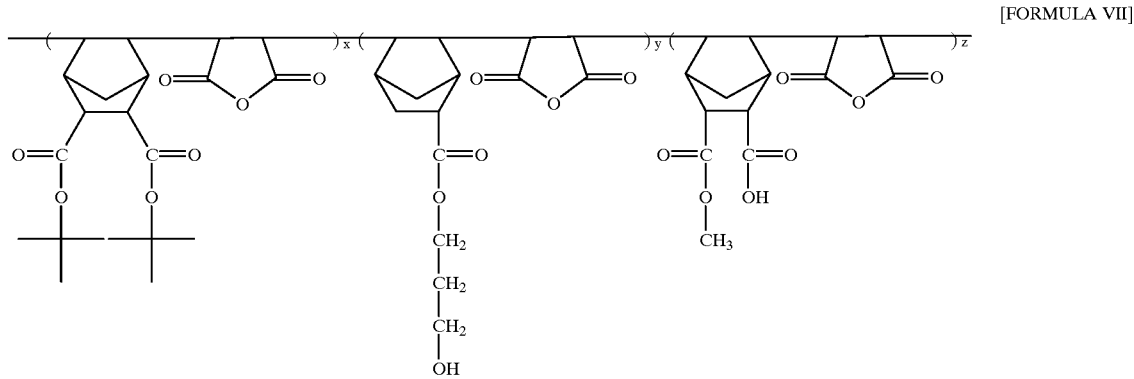

[FORMULA VII]

wherein, the ratio x:y:z is (0.001–99%): (0–99%): (0–99%).

The copolymer resin of Formula IV can be prepared according to the present invention by reacting 2,2-di-t-butyl-5-norbornene-2,3-dicarboxylate, 2-hydroxyethyl-5-norbornene-2-carboxylate, maleic anhydride and 5-norbornene-2-carboxylic acid in the presence of a conventional polymerization initiator, as below illustrated in Reaction Scheme I.

SCHEME I

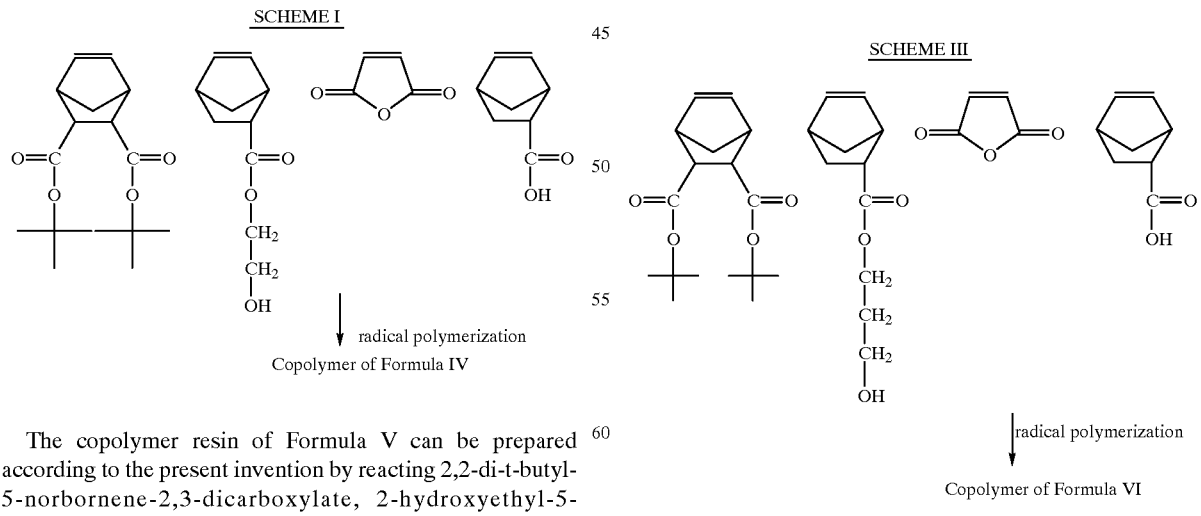

Copolymer of Formula IV

The copolymer resin of Formula V can be prepared according to the present invention by reacting 2,2-di-t-butyl-5-norbornene-2,3-dicarboxylate, 2-hydroxyethyl-5-norbornene-endo-2,3-dicarboxylic acid, maleic anhydride and mono-methyl cis-5-norbornene-endo-2,3-dicarboxylic acid in the presence of a conventional polymerization initiator, as below illustrated in Reaction Scheme II.

SCHEME II

Copolymer of Formula V

The copolymer resin of Formula VI can be prepared according to the present invention by reacting 2,2-di-t-butyl-5-norbornene-2,3-dicarboxylate, 2-hydroxypropyl-5-norbornene-2-carboxylate, maleic anhydride and 5-norbornene-2-carboxylic acid in the presence of a conventional polymerization initiator, as below illustrated in Reaction Scheme III.

SCHEME III

Copolymer of Formula VI

The copolymer resin of Formula VII can be prepared according to the present invention by reacting 2,2-di-t-butyl-5-norbornene-2,3-dicarboxylate, 2-hydroxypropyl-5- norbornene-2-carboxylate, maleic anhydride and monomethyl cis-5-norbornene-endo-2,3-dicarboxylic acid in the presence of a conventional polymerization initiator, as below illustrated in Reaction Scheme IV.

SCHEME IV

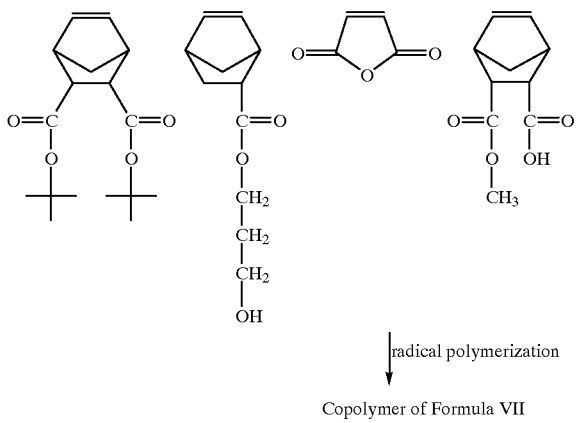

↓ radical polymerization

Copolymer of Formula VII

The aforementioned copolymer resins (Formulas IV to VII) can be prepared according to the present invention by a conventional polymerization process such as bulk polymerization or solution polymerization. Preferred polymerization initiators used in the present invention include benzoyl peroxide, 2,2'-azobisisobutyronitrile(AIBN), acetylperoxide, laurylperoxide, tert-butylperacetate, di-t-butyl peroxide, or the like. As a solvent, cyclohexanone, methyl ethyl ketone, benzene, toluene, dioxane, and/or dimethylformamide may be used individually, or in a mixture.

In the process for preparing the copolymer resin according to the present invention, general polymerization conditions, including temperature and pressure of radical polymerization, may vary depending upon the properties of the reactants, but it is preferable to carry out the polymerization reaction at a temperature between 60° C. and 200° C. under nitrogen or argon atmosphere for 4 to 24 hours.

The copolymer resin photoresist composition according to the present invention can be prepared using a conventional process for forming a photoresist composition; that is, by mixing the resin with a conventional photoacid generator in the presence of an organic solvent to form a photoresist solution. This photoresist composition can be used in the formation of a positive micro-image. In the process of forming a photoresist pattern on a semiconductor element, the amount of the copolymer resin depends on the organic solvent or photoacid generator used, and the conditions of lithography, but conventionally it is about 10 to 30% by weight of the organic solvent used.

The process for forming a photoresist pattern of a semiconductor element by using the copolymer resin according to the present invention is described in detail hereinbelow:

The copolymer resin of the present invention is preferably dissolved in cyclohexanone at a concentration of 10 to 30% by weight. An onium salt or organic sulfonic acid (0.1 to 10% by weight of copolymer resin) is preferably added to the copolymer resin solution as an photoacid generator. The mixture is filtered through an ultra-micro filter to prepare the photoresist solution. Preferred photoacid generators include triphenylsulfoniumtriflate, dibutylnaphtylsulfoniumtriflate, 2,6-dimethylsulfonate, bis(arylsulfonyl)-diazomthane, oximsulfonate, 2,1-diazonaphthoquinone-4-sulfonate, and the like.

Preferred organic solvents other than cyclohexanone, include ethyl 3-ethoxypropionate, methyl 3-methoxypropionate, propyleneglycol methyl ether acetate, and the like. It is preferable to use the solvent in a quantity equal to 200 to 1000 wt % of the photoresist resin used in the preparation.

The photoresist solution is preferably spin-coated on a silicon wafer to form a thin film, and the coated wafer is then prebaked in an oven or on a hot plate at 80° C.–150° C. for 1–5 minutes, exposed to light by using a far ultraviolet exposer or an eximer laser exposer, and post-heated at 100° C.–200° C. for 1 second to 5 minutes. The exposed wafer is impregnated with 2.38% aqueous TMAH solution for 1–1.5 minutes to obtain a positive resist pattern.

The light source used to expose the photoresist can be ArF, KrF, E-beam, EUV (extreme ultraviolet), ion beam, or the like. Preferred light energy for exposure is 0.1–10 mJ/cm2.

A better understanding of the present invention may be obtained by reference to the following examples which are set forth to illustrate, but are not to be construed to limit, the present invention.

PREPARATION EXAMPLE I

Synthesis of 2,3-di-t-butyl-5-norbornene-2,3-dicarboxylate

Cyclopentadiene (22 g) and tetrahydrofuran solvent (150 g) are charged in a reactor and stirred to form a homogeneous mixture. To the reaction mixture, 1,4-di-t-butyl fumalate (70 g) is added, and the resultant mixture is stirred at a temperature between 20° C. and 80° C. for about 10 hours to carry out the reaction. When the reaction is completed, the solvent is removed by using a rotary evaporator, and the residue is distilled under reduced pressure to obtain 72 g (yield: 74%) of 2,3-di-t-butyl-5-norbornene-2,3-dicarboxylate.

PREPARATION EXAMPLE II

Synthesis of 2-hydroxyethyl-5-norbornene-2-carboxylate

Cyclopentadiene (66 g) and acrylic acid (86 g) are charged in a reactor and the mixture is dissolved in tetrahydrofuran solvent (500 g). The resultant mixture is reacted at 30° C. for about 24 hours. Then, the solvent is removed by using a rotary evaporator, and the residue is distilled under reduced pressure to obtain 148 g (yield: 72%) of 2-hydroxyethyl-5-norbornene-2-carboxylate.

PREPARATION EXAMPLE III

Synthesis of 2-hydroxypropyl-5-norbornene-2-carboxylate

The same procedure described in Preparation Example II is repeated but 3-hydroxypropylacrylate (152 g) is used instead of 2-hydroxyethylacrylate to give 156 g (yield: 74%) of 3-hydroxypropyl-5-norbornene-2-carboxylate.

PREPARATION EXAMPLE IV

Synthesis of 5-norbornene-2-carboxylic Acid

Cyclopentadiene (66 g) and acrylic acid (86 g) are charged in a reactor and the mixture is dissolved in tetrahydrofuran solvent (500 g). The resultant mixture is reacted at 30° C. for about 24 hours. Then, the solvent is removed by using a rotary evaporator, and the residue is distilled under reduced pressure to obtain 110 g (yield: 71%) of 5-norbornene-2-carboxylic acid.

PREPARATION EXAMPLE V

Synthesis of Mono-methyl Cis 5-norbornene-endo-2,3-dicarboxylate

Cyclopentadiene (66 g) and tetrahydrofuran solvent (500 g) are charged in a reactor and the mixture is stirred homogeneously. To the reaction mixture, maleic anhydride (98 g) is added, and the resultant mixture is stirred at 0° C. for about 12 hours. Then, the mixture is filtered to remove the precipitate. To the resultant reactant, a 10% aqueous NaOH solution is added to carry out a hydrolysis reaction. The reactant is neutralized by using a 10% sulfuric acid solution. When reaction is completed, the resultant product is recovered by filtration and dried to obtain 150 g (yield: 86%) of mono-methyl cis 5-norbornene-endo-2,3-dicarboxylate.

EXAMPLE I

Synthesis of Poly[2,3-di-t-butyl-5-norbornene-2,3-dicarboxylate/2-hydroxyethyl-5-norbornene-2-carboxylate/maleic Anhydride/5-norbornene-2-carboxylic acid] Copolymer Resin (Formula IV)

Maleic anhydride (1 mol); 2,3-di-t-butyl-norbornene-2,3-dicarboxylate (0.5–0.9 mol) prepared according to Preparation Example I; 2-hydroxyethyl-5-norbornene-2-carboxylate (0.05–0.8 mol) prepared according to Preparation Example II; and 5-norbornene-2-carboxylate (0.01–0.5 mol) prepared according to Preparation Example IV are dissolved in tetrahydrofuran or toluene. Then, 2,2'-azobisisobutyronitrile(AIBN) (0.5–10 g), is added thereto as a polymerization initiator and the reaction is performed at a temperature between 65° C. and 70° C. under nitrogen or argon atmosphere for 4–24 hours. Crude product thus obtained is precipitated from ethyl ether or hexane, and the precipitate is dried to give 58 g of the subject copolymer resin (Formula IV) having a molecular weight 3,000–100,000 (yield: 80%). The copolymer resin thus prepared has high transparency to ArF light, increased etching resistance and excellent adhesiveness, is developable by 2.38 wt % aqueous TMAH solution and is capable of mass production.

EXAMPLE II

Synthesis of Poly[2,3-di-t-butyl-5-norbornene-2,3-dicarboxylate/2-hydroxyethyl-5-norbornene-2-carboxylate/maleic Anhydride/mono-methyl-cis-5-norbornene-endo-2,3-dicarboxylate] Copolymer Resin (Formula V)

The same procedure described in Example I is repeated but mono-methyl cis-5-norbornene-endo-2,3-dicarboxylate (10 g) prepared according to Preparation Example V was used instead of 5-norbornene-2-carboxylic acid, to obtain 62 g of the subject copolymer resin (Formula V) having a molecular weight of 3,000–100,000 (yield: 81%). The copolymer resin thus prepared has similar properties to the resin of Example I. However, the problem of offensive odor with the resin of Example I is solved by introducing the mono-methyl cis-5-norbornene-endo-2,3-dicarboxylate unit in the copolymer resin.

EXAMPLE III

Synthesis of Poly[2,3-di-t-butyl-5-norbornene-2,3-dicarboxylate/3-hydroxypropy-5-norbornene-2-carboxylate/maleic anhydride/5-norbornene-2-carboxylic acid] Copolymer Resin (Formula VI)

The same procedure as described in Example I is repeated but 3-hydroxypropyl-5-norbornene-2-carboxylate (20 g) prepared according to Preparation Example III is used instead of 2-hydroxyethyl-5-norbornene-2-carboxylate, to obtain 60 g of the subject copolymer resin (Formula VI) having a molecular weight of 4,000– 100,000 (yield: 79%). In the copolymer resin thus prepared, the number of carbon atoms in the chain having a hydrophilic group(—OH) is increased to three by introducing 3-hydroxypropyl-5-norbornene-2-carboxylate, and, as a result, the copolymer resin has increased chain flexibility and excellent adhesiveness.

EXAMPLE IV

Synthesis of poly[2,3-di-t-butyl-5-norbornene-2,3-dicarboxylate/3-hydroxypropyl-5-norbornene-2-carboxylate/maleic anhydride/mono-methyl cis-5-norbornene-endo-2,3-dicarboxylate] copolymer resin (Formula VII)

The same procedure as described in Example I is repeated but mono-methyl cis-5-norbornene-endo-2,3-dicarboxylate (10 g) prepared according to Preparation Example V is used instead of 5-norbornene-2-carboxylic acid, to obtain 62 g of the subject copolymer resin (Formula V) having a molecular weight of 3,000–100,000 (yield: 80%). The copolymer resin thus prepared has similar properties to the resin of Example III, but the problem of the monomer's offensive odor is solved. Thus, the copolymer resin can be manufactured on a large scale.

EXAMPLE V

Synthesis of Photoresist and Formation of Pattern

A copolymer resin of the present invention (Formulas IV to VII) (10 g), prepared according to Examples I to IV, is dissolved in 3-methoxymethylpropionate solvent (40 g), and triphenylsulfonium triflate or dibutylnaphtylsulfonium triflate (about 0.2–1 g) is added thereto as a photoacid generator. After stirring, the mixture is filtered to give a photoresist solution. Then, the photoresist solution is spin-coated on a surface of a wafer to provide a thin film, and the wafer is soft-baked in an oven or on a hot plate at 70° C.–150° C. for 1–5 minutes. After exposing, to 250 nm wavelength light by using an exposer, it is post-baked at 90° C.–160° C. In this case, the above soft-bake and post-bake steps may also be carried out at a temperature between 70° C. and 200 C.

Then, the exposed wafer is impregnated for 1.5 minutes with an aqueous TMAH solution having a concentration of 0.01–5% by weight as a developing solution, to obtain an ultra-micro photoresist pattern (resolution: 0. 13 $\mu$m).

By introducing the 2,3-di-t-butyl-5-norbornene-2,3-dicarboxylate unit into the structure of a norbornene-maleic anhydride copolymer, the copolymer resin of the present invention is easily prepared by conventional radical polymerization, has high transparency at 193 nm wavelength, provides increased etching resistance, prevents the top loss phenomenon, enhances adhesive strength due to increasing protection ratio in the copolymer resin, and shows an excellent resolution of 0. 13 $\mu$m.

Many modifications and variations of the present invention are possible in light of the above teachings. Therefore, it is to be understood that within the scope of the appended claims, the invention may be practiced otherwise than as specifically described.

What is claimed is:

1. A photoresist copolymer consisting essentially of:

(i) a monomer having the following Formula III:

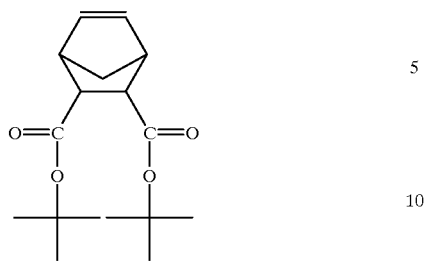

(ii) at least one other norbornene monomer; and
(iii) maleic anhydride.

2. A photoresist copolymer in accordance with claim 1 wherein said other norbornene monomer comprises 2-hydroxyethyl-5-norbornene-2-carboxylate or 2-hydroxypropyl-5-norbornene-2-carboxylate.

3. A photoresist copolymer in accordance with claim 1 wherein said other norbornene monomer comprises 5-norbornene-2-carboxylic acid or mono-methyl cis-5-norbornene-endo-2,3-dicarboxylate.

4. A photoresist copolymer in accordance with claim 1 selected from the group consisting of copolymers represented by the following Formulas IV to VII:

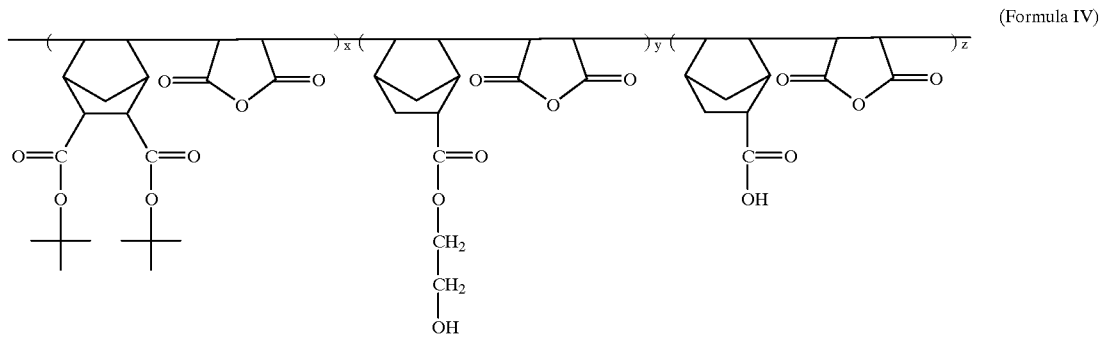
(Formula IV)

wherein, the ratio x:y:z: is (0.001–99%): (0–99%): (0–99%);

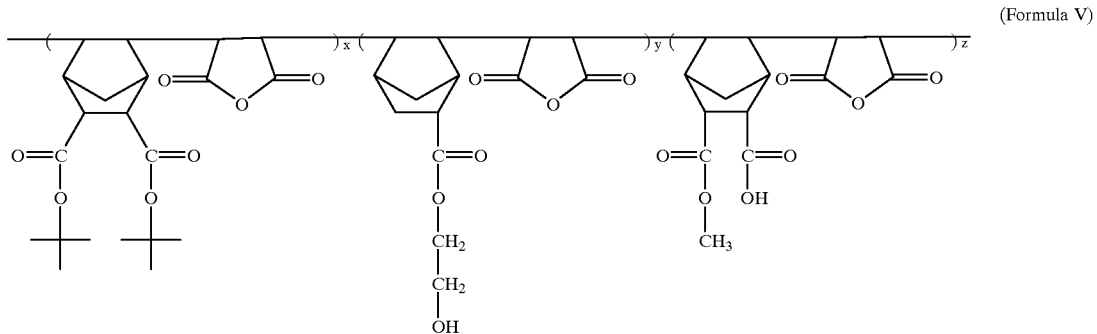
(Formula V)

wherein, the ratio x:y:z: is (0.001–99%): (0–99%): (0–99%);

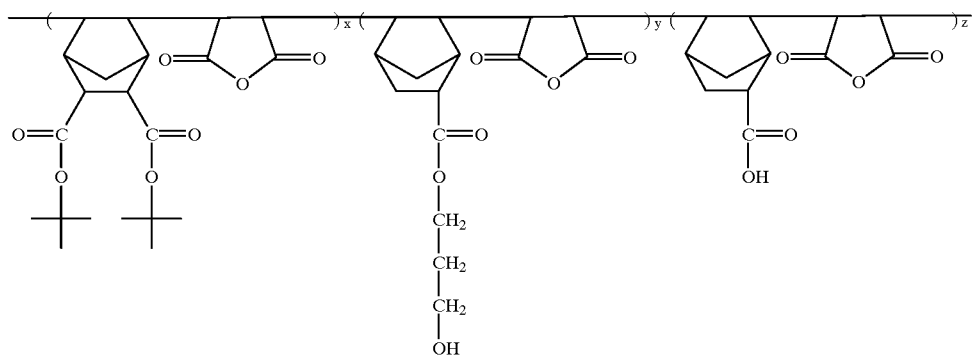

(Formula VI)

wherein, x is a mole % of 0.5–99%, and y and z are independently a mole % of 0.1–99%; and

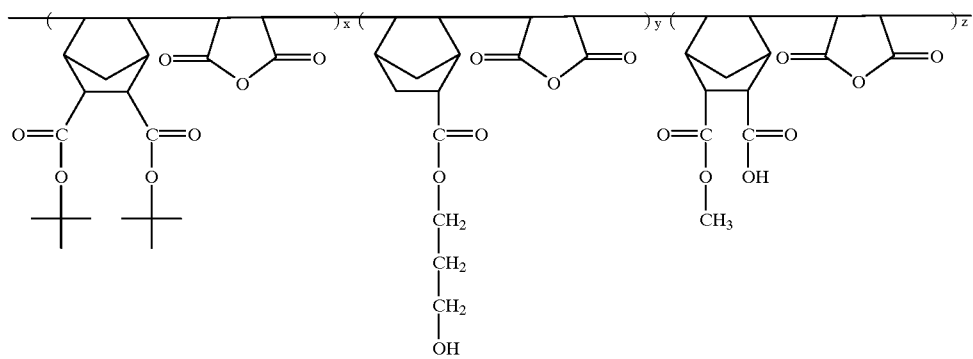

(Formula VII)

wherein, the ratio x:y:z: is (0.001–99%): (0–99%): (0–99%).

5. A photoresist copolymer in accordance with claim 4 having a molecular weight of 3,000 to 100,000.

6. A process for preparing a photoresist copolymer which comprises introducing a 2,3-t-butyl-5-norbornene-2,3-dicarboxylate unit into a norbornene-maleic anhydride copolymer structure.

7. A process for preparing a photoresist copolymer in accordance with claim 6 wherein said introduction is accomplished by free radical polymerization in a solvent using a polymerization initiator.

8. A process for preparing a photoresist copolymer in accordance with claim 7 wherein the polymerization initiator is benzoyl peroxide, 2,2'-azobisisobutyronitrile, acetyl peroxide, lauryl peroxide, t-butyl acetate or di-t-butyl peroxide.

9. A process for preparing a photoresist copolymer in accordance with claim 7 wherein the solvent is cyclohexanone, methyl ethyl ketone, benzene, toluene, dioxane, dimethylformamide or mixtures thereof.

10. A process for preparing a photoresist copolymer in accordance with claim 6 wherein said norbornene-maleic anhydride copolymer structure contains 2-hydroxyethyl-5-norbornene-2-carboxylate or 2-hydroxypropyl-5-norbornene-2-carboxylate.

11. A process for preparing a photoresist copolymer in accordance with claim 6 wherein said norbornene-maleic anhydride copolymer structure contains 5-norbornene-2-carboxylic acid or mono-methyl cis-5-norbornene-endo-2,2-dicarboxylate.

12. A photoresist composition comprising the copolymer of claim 11 and a photoacid generator in an organic solvent.

13. A photoresist composition in accordance with claim 12 wherein the copolymer is poly[2,3-di-t-butyl-5-norbornene-2,3-dicarboxylate/2-hydroxyethyl-5-norbornene-2-carboxylate/maleic anhydride/5-norbornene-2-carboxylic acid]; poly[2,3-di-t-butyl-5-norbornene-2,3-dicarboxylate/2-hydroxyethyl-5-norbornene-2-carboxylate/maleicanhydride/mono-methyl cis 5-norbornene-endo-2,3-dicarboxylate]; poly[2,3-di-t-butyl-5-norbornene-2,3-dicarboxylate/3-hydroxypropyl-5-norbornene-2-carboxylate/maleic anhydride/5-norbornene-2-dicarboxylic acid]; or poly[2,3-di-t-butyl-5-norbornene-2,3-dicarboxylate/3-hydroxypropyl-5-norbornene-2-carboxylate/maleic anhydride/mono-methyl cis 5-norbornene-endo-2,3-dicarboxylate].

14. A photoresist composition in accordance with claim 12 wherein the photoacid generator is triphenyl sulfonium triflate or dibutyl naphthyl sulfonium triflate.

15. A photoresist composition in accordance with claim 12 wherein the organic solvent is ethyl 3-ethoxypropionate, methyl 3-methoxypropionate, cyclohexanone or propyleneglycol methyl ether acetate.

* * * * *

UNITED STATES PATENT AND TRADEMARK OFFICE
CERTIFICATE OF CORRECTION

PATENT NO. : 6,348,296 B1  
DATED : February 19, 2002  
INVENTOR(S) : Min Ho Jung, Cha Won Koh and Hyung Gi Kim It is certified that error appears in the above-identified patent and that said Letters Patent is hereby corrected as shown below:

Column 4,  
Line 41, please insert the phrase -- Formula VII -- after the term "following".

Column 9,  
Line 63, the term "hydroxypropy" should read -- hydroxypropyl --.

Column 10,  
Line 42, please delete a comma after the term "exposing".  
Line 51, the "0. 13" should read -- 0.13 --.  
Line 60, the "0. 13" should read -- 0.13 --.

Column 14,  
Line 40, the term "claim 11" should read -- claim 1 --.

Signed and Sealed this

Fifteenth Day of April, 2003

JAMES E. ROGAN  
*Director of the United States Patent and Trademark Office*